Figure 1:
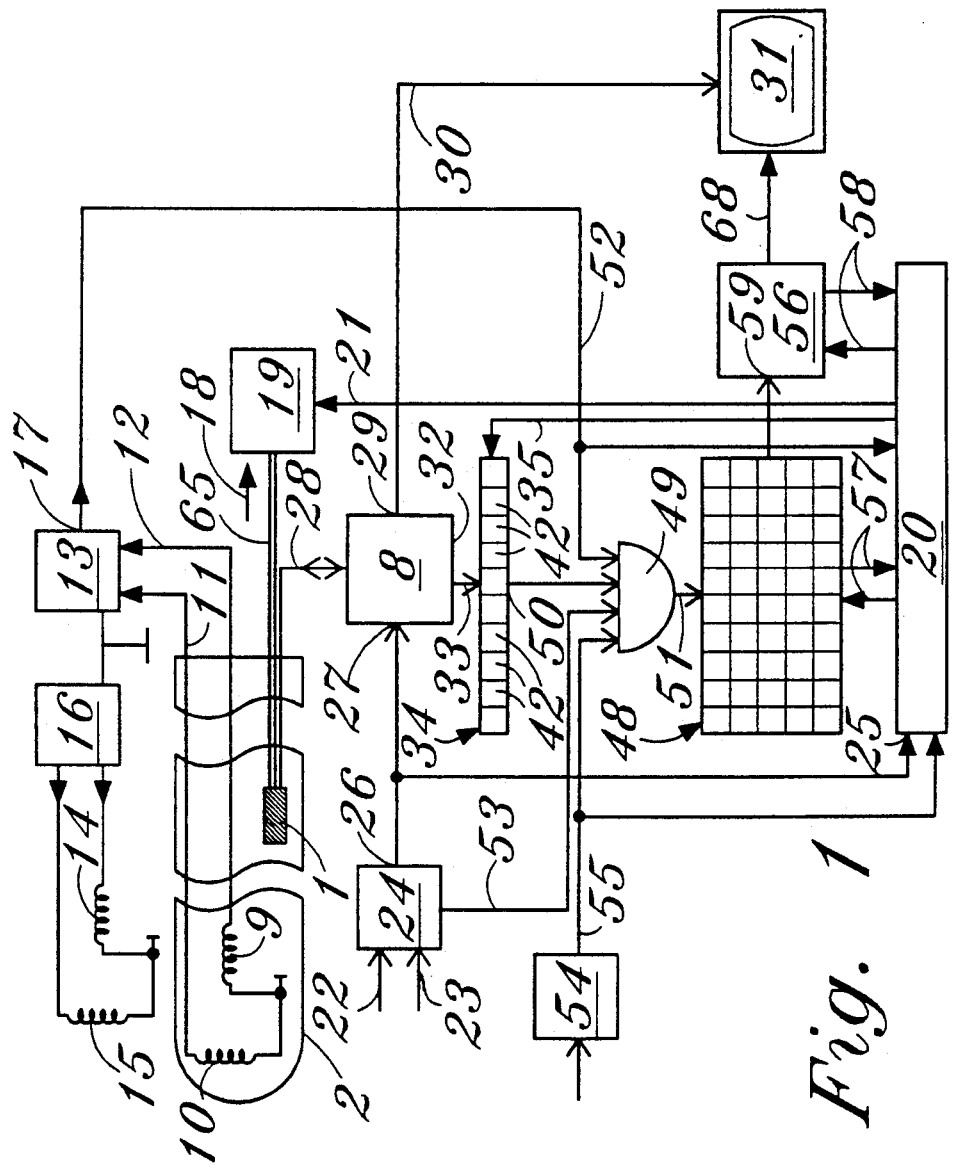

United States Patent [19]

Wollschläger et al.

[11] Patent Number: 5,295,486
[45] Date of Patent: Mar. 22, 1994

[54] TRANSESOPHAGEAL ECHOCARDIOGRAPHY DEVICE

[76] Inventors: Helmut Wollschläger, Kartäuserstrasse 134; Susanna Wollschläger, Laufenerstrasse 15; Andreas Zeiher, Klarastrasse 55, all of D-7800 Freiburg; Hans-Peter Klein, An der Weinleite 12b, D-8017 Ebersberg, all of Fed. Rep. of Germany

[21] Appl. No.: 768,897
[22] PCT Filed: Aug. 23, 1989
[86] PCT No.: PCT/DE89/00550
 § 371 Date: Oct. 18, 1991
 § 102(e) Date: Oct. 18, 1991
[87] PCT Pub. No.: WO90/13259
 PCT Pub. Date: Nov. 15, 1990

[30] Foreign Application Priority Data

May 3, 1989 [DE] Fed. Rep. of Germany ....... 3914619

[51] Int. Cl.$^5$ ............................................. A61B 8/12
[52] U.S. Cl. ................................. 128/661.01; 128/916; 128/661.04
[58] Field of Search ............... 128/660.09, 661.01, 128/661.08, 660.07, 661.04, 916

[56] References Cited

U.S. PATENT DOCUMENTS

| | | | |
|---|---|---|---|
| 3,805,596 | 4/1974 | Klahr | 128/660.09 |
| 4,637,256 | 1/1987 | Sugiyama et al. | 128/660.09 |
| 4,821,728 | 4/1989 | Ledley | 128/661.01 |
| 5,054,492 | 10/1991 | Scribner et al. | 128/660.09 |
| 5,086,776 | 2/1992 | Fowler, Jr. et al. | 128/661.08 |

*Primary Examiner*—Francis Jaworski
*Assistant Examiner*—George Manuel
*Attorney, Agent, or Firm*—Michael J. Hughes

[57] ABSTRACT

In a device for transoesophagal echocardiography, an ultrasound transformer (1) is used to make a sequence of layer images for a plurality of parallel sectional planes with the aid of an ultrasonic diagnostic device (8). The layer images made during one cardiac cycle with the image repetition rate of the ultrasonic diagnostic device (8) are stored in a buffer store (34) and transferred to a main store (48) with the aid of a selection stage (49) to generate three-dimensional sets of images only when a locating device (13), and ECG device (24) and a respiration detector (54) generate release signals which are allocated to a constant spatial probe position, a constant R—R interval distance and a constant respiratory state. The content of the main store (48) is evaluated with the aid of an image processing system (56), whereby sectional images may be calculated, especially for any sectional plane, and displayed on a monitor (31).

10 Claims, 4 Drawing Sheets

TRANSESOPHAGEAL ECHOCARDIOGRAPHY DEVICE

The invention is a transesophageal echocardiography device with a flexible ultrasound probe with an attached ultrasound transducer for the generation of multiplanar images of a patients' heart, which is connected to an image processing system via a control and evaluation device.

A transesophageal echocardiography device described in Roy W. Martin et al., An Endoscopic Micromanipulator for Multiplanar Transesophageal Imaging, Ultrasound in Med. and Biol. Vol. 12, Nr. 12, pp. 965-975, 1986 and produces three-dimensional reconstructions of a cardiac ultrasound image by recording a multitude of sectional images with the help of an ultrasound transducer attached to the front of an endoscope. The transducer can be swung horizontally around the longitudinal axis of the endoscope producing a multitude of tomograms whose assigned section planes run diagonal to each other. This affects the geometrical and optical qualities of the image data received, resulting in inferior quality, a small, unfavorably distributed scanning volume. Furthermore, the scans cannot be reproduced, making it impossible to achieve the three-dimensional image quality necessary for comparative studies.

An essay by Michael Schlüter et al., Transesophageal Two-Dimensional Echocardiography: Comparison of Ultrasonic and Anatomic Sections, The American Journal of Cardiology, Vol. 53, pp. 1173-1178, 1984, describes a transesophageal echocardiography device which generates horizontal tomograms. Tomographic sections through the heart are generated by moving and turning a gastroscope within the esophagus. The necessity of manually moving the gastroscope—a movement which cannot be reproduced—makes it impossible to generate three-dimensional plastic images from two-dimensional tomograms.

U.S. Pat. No. 4,327,738 describes an endoscopic process and device for ultrasound-B-image scans. The ultrasound transducer is attached to the rigid front part of an otherwise flexible tube. A difficult-to-reproduce re-positioning is required to produce multiplanar tomograms, making exact three-dimensional reconstructions of the scanned organs impossible.

Starting from said technology, the invention's purpose is to create a transesophageal echocardiography device for the generation of reproducible topographic information about the heart and its movements.

The invention solves this task with the help of the following innovations: an ultrasound transducer for scanning a series of parallel section planes of the heart is attached to a sliding rail progressively moved axially along a straight line inside the ultrasound endoscopy device; a temporary memory allows for the storage of at least one tomogram when scanning each section synchronous with the cardiac phases; a main memory for at least one three-dimensional image composed of a series of parallel tomograms is used, whose data input port is connected to the data output port of the temporary memory via one selection option through which the individual tomograms associated with consecutive cardiac cycles of a series of parallel tomograms can only be transferred to the main memory if the cardiac cycles are of the same length; and an advance signal will not move the ultrasound transducer into the next section until the temporary memory data are transferred to the main memory.

The progressive movement of the ultrasound transducer along a straight line leads to the generation of parallel section planes and equally parallel tomograms. The ultrasound transducer is located on a sliding rail in the distal end of the ultrasound endoscopy device (an esophagus probe) and can be moved axially. The esophagus probe is flexible to facilitate insertion into the esophagus in the course of transesophageal echocardiography. However, the distal end is stiff, in order to precisely orient the scanning planes. This is achieved with the help of a multitude of guiding links, which are pulled face to face before scanning the section planes. When stiff, these guiding links links form a straight and stable guide canal in which the sliding rail with the ultrasound transducer can be moved gradually along a straight line.

A manipulation device is planned for moving the sliding rail as well as for stiffening the distal end of the esophagus probe. This device includes an intermittent motor whose forward motion is synchronized by evaluating an ECG.

The device has a memory storage buffer, which allows for the storage of a multitude of tomograms belonging to the same section plane but different intervals or phases of a cardiac cycle. When the patient has a constant heart and respiration rate, and the location of the esophagus probe is stable, the tomograms stored in the temporary memory are transferred to the main memory, which combines the tomograms belonging to the same cardiac phases of consecutive cardiac cycles into three-dimensional image data sets. This means that the main memory contains a series of three-dimensional reconstructions of the heart or data cubes for each increment of axial advance by the ultrasound transducer in the esophagus in accordance with the chronological resolution of a cardiac cycle or the image repetition rate of the ultrasound device.

A selection option exists between intermediate and main memory to assure that only tomograms recorded under stable conditions are combined into three-dimensional image data sets. Only when the data contained in the memory storage buffer meet the necessary criteria for transfer into the main memory, is the sliding rail with the attached ultrasound transducer advanced by the intermittent motor and one can head for the adjacent section plane.

A practical model of the invention would contain a device for recording electrocardiograms, which would serve two purposes: it would synchronize the advance of the motor and synchronize or trigger the images per section plane which are produced at different times during a cardiac cycle. The recorded electrocardiogram furthermore helps to determine the time interval between the consecutive R waves of an ECG and to record and monitor a constant heart rate, i.e. cardiac cycles of constant length. This assures that the tomograms consecutively recorded within a fixed time grid are assigned to the same phases of a cardiac cycle. If the cardiac cycle were to become shorter due to the heart beating faster, for example, the $n^{th}$ tomogram would no longer be assigned to the originally assigned cardiac phase, but to a later phase, meaning that a three-dimensional image data set would contain tomograms which were recorded at different cardiac phases. However, such an image data set is unusable due to the movement of the heart.

The practical improvements and further developments of the invention are the subject of subordinate claims.

Following is a more detailed description of the invention with the help of a practical sample.

Figure 2:
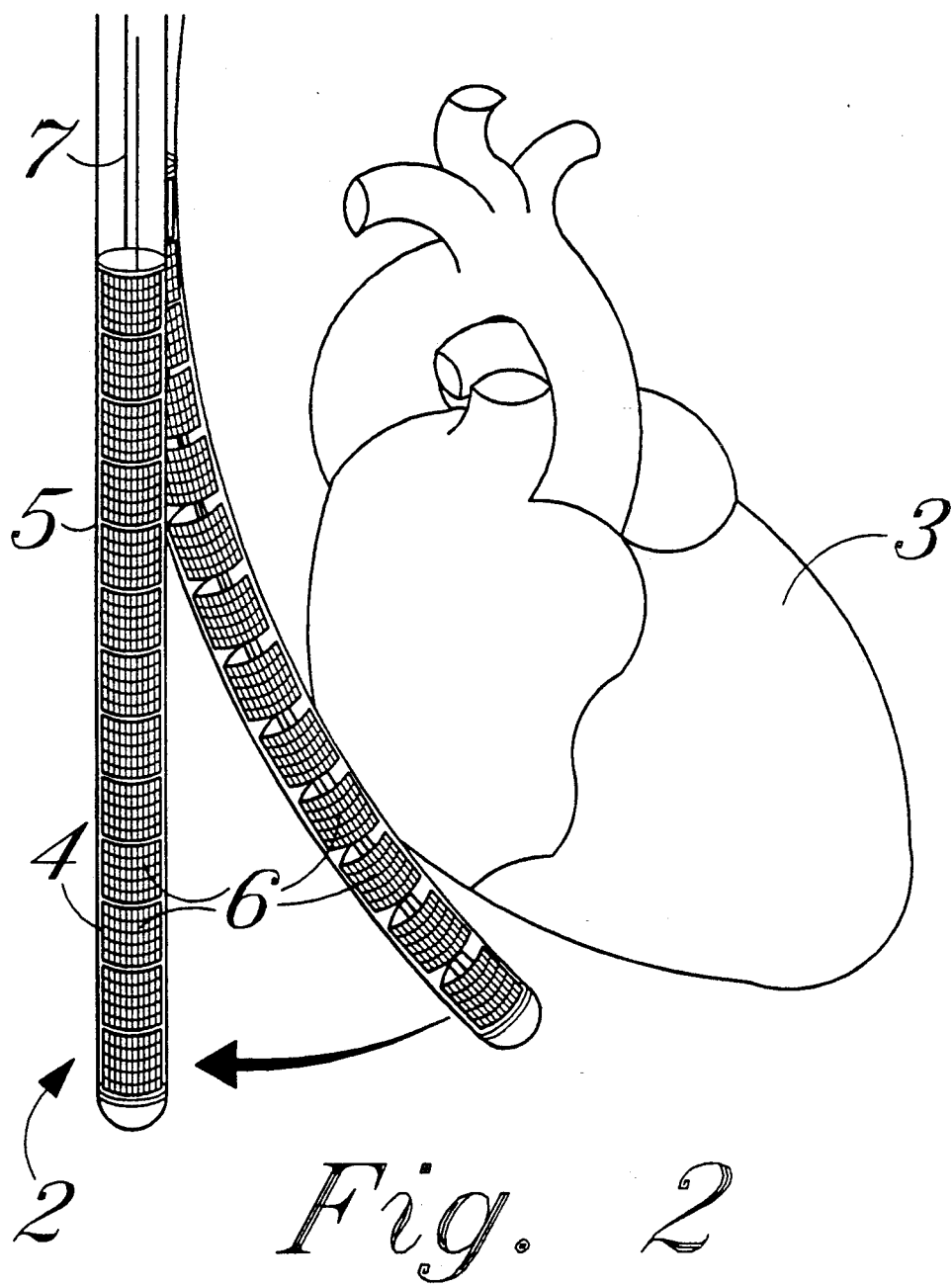
Figure 3:
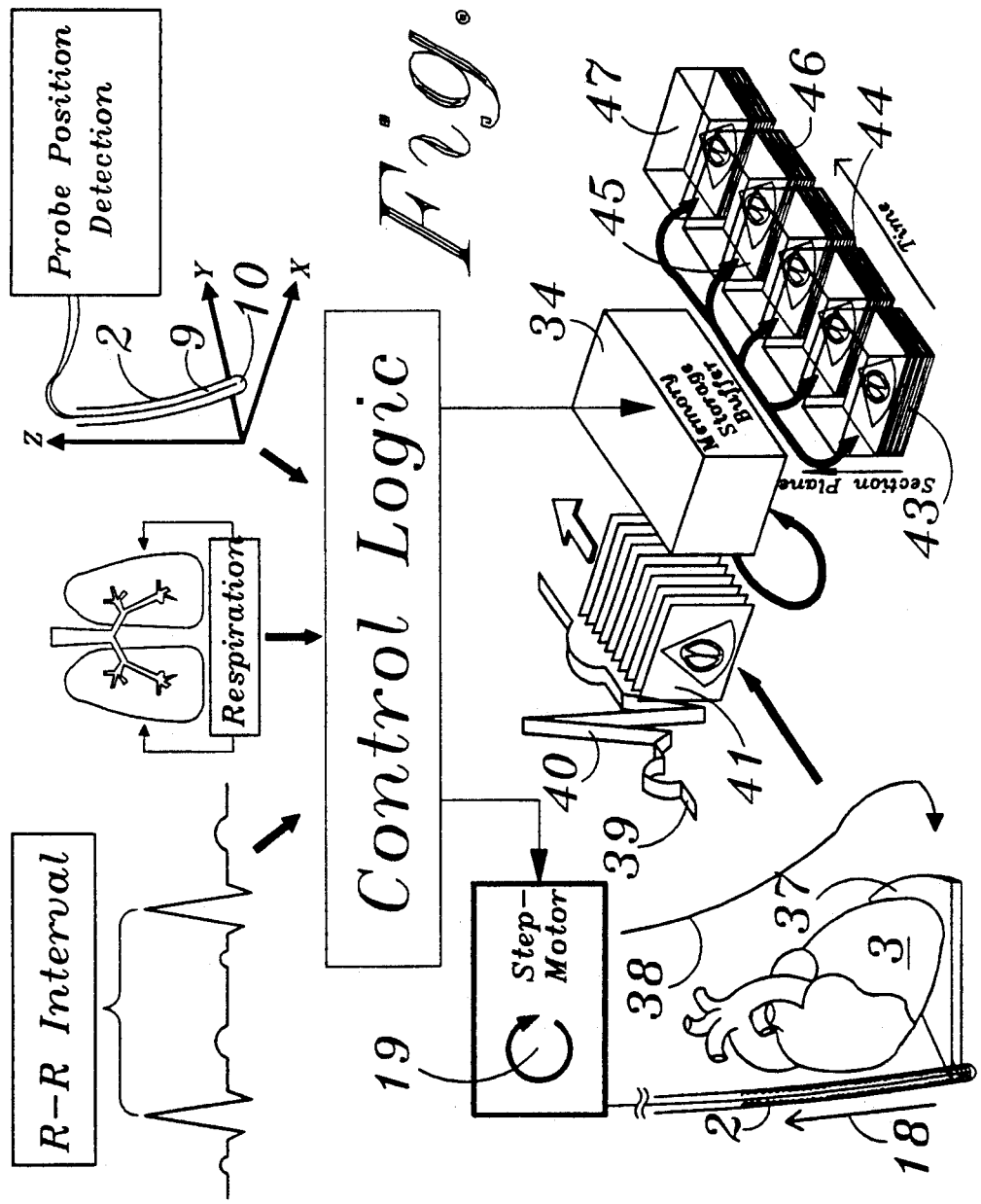
Figure 4:
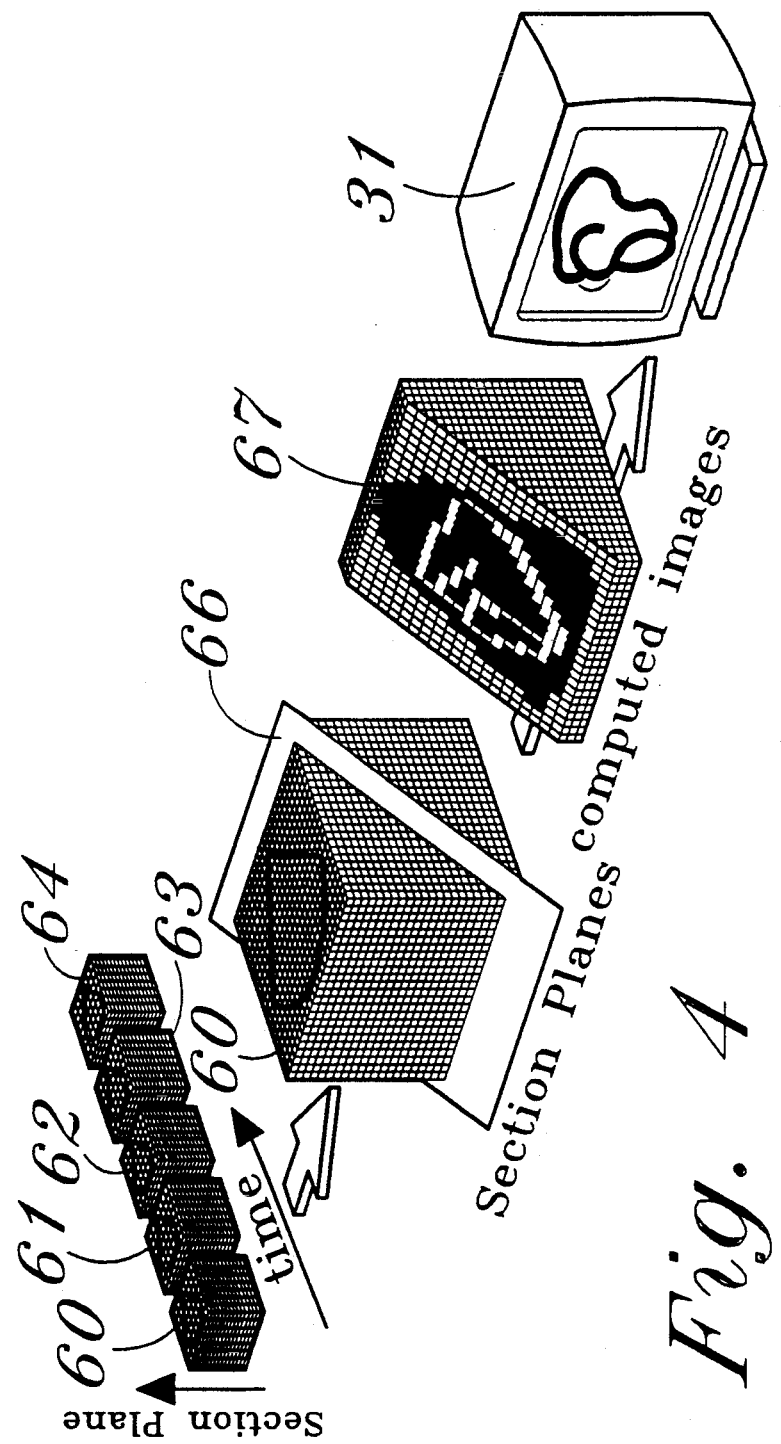

FIG. 1 shows a schematic representation of the invented device for transesophageal echocardiography, FIG. 2 shows a three-dimensional view of the esophagusscope or distal end of the endoscopic device in two different positions near the heart to be monitored, FIG. 3 shows a schematic and graphic illustration of the invention's operating logic and FIG. 4 shows a schematic depiction to illustrate the generation of an arbitrary section plane through a three-dimensional image of a heart.

The transesophageal echocardiography device depicted schematically in FIG. 1 is equipped with an ultrasound head (1), for example in the form of a mechanical sector scanner or phased array, which can be guided axially alongside the front end of an esophagus probe (2), which—together with a heart (3)—is depicted in two different positions in a simplified illustration in FIG. 2. The esophagus probe (2) has a distal end (4) with flexible tubing (5), which holds together a multitude of rigid guiding links (6). The distal end (4) can easily be bent due to the elasticity of the flexible tubing (5), as illustrated in FIG. 2 by the part of the esophagus probe (2) which is bent to the right.

On the inside of the guiding links (6), a guide canal was designed in which a sliding rail (not depicted in the illustration) with the attached ultrasound head (1) can be moved axially down the length of the canal. To guarantee the stretching and stiffening of the distal end (4) for a precise orientation of the scanning planes of the ultrasound head (1), the guiding links have 6 holes through which a tension wire (7) extends, which can be tightened with the help of a Bowden pull wire. This helps to press the individual guiding links (6) against each other to assure precise guidance of the sliding rail for the ultrasound head (1). When the guiding links (6) are tightened with the help of the tension wire (7), they are pressed together face-to-face as illustrated on the left side of FIG. 2, leading to a stiffening and alignment of the distal end (4) along a straight line. After aligning the distal end (4) as illustrated on the left side of FIG. 2, a multitude of tomograms corresponding to the section planes defined by the position of the esophagus probe (2) and ultrasound head (1) are recorded with the help of the ultrasound head (1) and the attacked ultrasound diagnostic device (8). This is done as soon as the patient has adjusted to the inserted esophagus probe (2) and his heart and respiration rate, and the position of the esophagus probe (2) are stable.

Since the position of the section planes through the heart (3) depends on the position of the esophagus probe (2), (which can be directly deduced from FIG. 2), a device for the detection of the probe's position within the patient's body is added to ensure that all section planes for the tomograms to be recorded and stored are truly parallel. This is achieved with the help of a longitudinal coil (9) and a cross coil (10), attached to one of the guiding links (6) or the front end of the esophagus probe (2) and further attached to a spatial coordinate detector (13) via two cables (11 and 12).

Both the longitudinal coil (9) and cross coil (10) are located within the field of two orthogonally oriented induction loops (14 and 15), which are alternately timed with the help of a pulse generator (16) in order to produce a stable system of coordinates and which induce different voltages with the help of the longitudinal coil (9) and the cross coil (10), depending on the position of the esophagus probe (2). These voltages are analyzed in the spatial coordinate detector (13).

The spatial coordinate detector (13) does not only locate the present position of the esophagus probe (2), but provides a continuous detection as well as a frequency analysis in regard to the different orientations and positions, so that a favored position or standardized direction can automatically be determined as soon as the patient has calmed down and the tomograms are being recorded.

At the output port of the spatial coordinate detector (13), a release signal is heard every time the desired most frequently used position of the esophagus probe (2) is achieved. At this most frequent or normally used position of the probe, the majority of recorded tomograms is usually generated from parallel section planes. The induction loops (14 and 15) are integrated into the patient's gurney, one of the induction loops being parallel to the plane formed by the surface of the gurney and the other one being integrated in a sidewall at a right angle to this plane. The induction loops (14 and 15) define a fixed three-dimensional system of coordinates, which is the point of reference for the position of the section plane which is being scanned with the help of the ultrasound head (1).

Each time a section plane or section of the heart is scanned and several tomograms have been generated for an assigned section or section plane at different phases of a cardiac cycle, the ultrasound head (1) is moved in the direction of an arrow (18) with the help of an intermittent motor (19). The intermittent motor (19) is connected to the rail carrying the ultrasound head (1) by a Bowden pull wire (65); this makes it possible to retract the ultrasound head (1) axially a distance of 0.5 mm after each cardiac cycle. This results in the generation of 210 section planes for a distance of 10.5 cm. These section planes are at right angles to the longitudinal axis of the esophagus probe (2) and go through the nearby heart (3). The forward motion of the intermittent motor (19) is synchronized with the ECG. The synchronization signals derived from the patient's ECG are generated by a computer (20) and transmitted via a synchronizing line (21) to the intermittent motor (19) and its electronic controls.

The patient's ECG is recorded with the help of electrodes (22, 23), which are connected to an ECG device (24). The ECG device (24) is connected to an ECG input port (25) on the computer (20), which also controls the components of the device shown in FIG. 1. The first output port (26) of the ECG device (24) is also connected to a control input port (27) of the ultrasound diagnostic device (8) to control the generation of multiplanar images by triggering the R waves in the ECG.

As soon as a trigger impulse is fed into the control input port (27), the ultrasound head (1) starts scanning the section plane assigned to the ultrasound head according to its position and orientation and in keeping with the image repetition rate of the ultrasound diagnostic device, in order to record tomograms (41) at different cardiac phases within a cardiac cycle (FIG. 3). To achieve this, the ultrasound head (1) is connected to the ultrasound diagnostic device (8) via a signalling line (28). At the first image output port (29) of the ultrasound diagnostic device (8), the individual tomograms (41) are found as signals and can be transferred to the monitor (31) via a video line (30). The monitor (31) allows for the continuous observation of the tomograms 41) which are depicted in quick succession. Depending on the individual ultrasound diagnostic device (8), the recording of a tomogram takes 13 msec., with the tomograms (41) shown at intervals of approx. 33 msec. For a cardiac cycle of 0.8 sec, approximately two dozen tomograms (41) can thus be recorded per cardiac cycle.

The second image output port (32) of the ultrasound diagnostic device (8) is connected to the data input port of a memory storage buffer (34) via a data line (33). Using an address line (35), the computer (20) selects the memory storage buffer locations in such a way that the tomograms (41) which are generated sequentially at different times within a cardiac cycle can be stored in the memory storage buffer (34) independent of the individual heart rate of the patient or his/her respiration and the position of the probe.

FIG. 3 illustrates in exploded view the functioning of the transesophageal electrocardiography devices shown in FIG. 1 in modular mimic display. Next to the heart (3), one can see the esophagus probe (2) and the ultrasound head (1) which can be moved in the direction of the arrow (18), thus allowing the scanning of sectors of the parallel section planes (36,37). An arrow (38) marks the difference between the section planes (36 and 37) after starting the intermittent motor (19), which is connected to the sliding rail carrying the ultrasound head (1) by a Bowden pull wire.

Using the control logic stored in the computer (20), the transesophageal echocardiography device's components depicted in FIG. 1 function as depicted in FIG. 3.

In FIG. 3, one can see the wave pattern (39) of an ECG and especially the R wave (40), which occurs at the beginning of a cardiac cycle. Tomograms (41), which are assigned to the section plane (37) at different intervals or cardiac phases of a cardiac cycle as illustrated in FIG. 3, are recorded every 30 or 33 msec. during a cardiac cycle with the help of the ultrasound head (1) and ultrasound diagnostic device (8). The tomograms (41)—depicted in schematic view in FIG. 3—whose number varies between 1 and several dozen, are transferred to the memory storage buffer (34) with the help of the computer's (20) control logic, with the address line (35) releasing memory areas (42) sequentially assigned to individual tomograms (41).

Since the tomograms (41) of a section plane, especially of section plane 37, were recorded at different times or phases of a cardiac cycle, they are distributed to data cubes (43 to 47) as illustrated in FIG. 3. These data cubes are implemented by the main memory (48). FIG. 3 illustrates how the tomograms (41), recorded at different times of a cardiac cycle but belonging to the same section plane, are distributed to the data cubes (43 to 47) of the main memory (48) by the memory storage buffer (34). One can see that, after a complete scan of the heart volume, the data cubes (43 to 47) contain complete, three-dimensional images which were generated by combining tomograms (41). During this process, each data cube (43 to 47) is assigned a different cardiac phase within a cardiac cycle. Even though the ultrasound diagnostic device (8) does not allow for the complete scanning of the total heart (3) volume within a period of time neglectable compared to the heart's movement, each data cube (43 to 47) contains a three-dimensional still image of the complete heart.

In the present example, it was assumed that no changes occurred in regard to the orientation of the esophagus probe (2), the heart and respiration rate of the patient during a number of cardiac cycles corresponding to the number of tomograms (41) in one of the data cubes (43 to 47). Since this is impossible to achieve in practical operation, the selection option (49) depicted in FIG. 1 was added to the control logic depicted schematically in FIG. 3.

The selection option (49) connects the output (50) of the memory storage buffer (34) to the data input (51) of the main memory (48). If the selection option (49) is turned on, the tomograms (41) stored in the memory areas (42) are sequentially transferred to the data cubes (43 to 47), depicted in schematic view. However, should there be no release signal at the output port (17) of the spatial coordinate detector (13), the selection option (49) is blocked with the help of the ultrasound diagnostic device (8) and stored in the memory storage buffer (34). The memory storage buffer 34) keeps on being overwritten with a new set of tomograms (41) until the selection option allows to switch through to the main memory (48).

The ECG device (24) is also connected to an assigned input port of the selection option (49) by a release line (53). The release line (53) is only active if the ECG device (24) has established that the R—R interval has remained constant within a tolerance of ± 5%. The ECG device (24) establishes automatically at which interval length there should be a release. This release should occur particularly if the patient's respiration is regular and his medium heart rate is stable, approximately one minute after insertion of the esophagus probe.

A respiration detector (54), which can be connected to the ECG device (24), supervises the patient's respiration curve and generates a release signal for the selection option (49) using another release line (55) when the patient's respiration rate is stable.

The above observations show that the data are only transferred from the memory storage buffer (34) to the main memory (48) if the R—R interval, the patient's respiration and the position of the probe are stable.

FIG. 1 shows furthermore that the computer's (20) task is to admit the output signals of the detection device (13), the ECG device (24) and the respiration detector (54). The computer (20) controls the order of the functions of the transesophageal echocardiography device shown in FIG. 1 by analyzing the different input signals.

The main memory (48) and the computer (20) are connected to a digital image processing system (56), as illustrated in FIG. 1. The control lines (57 and 58) connect the computer (20) to the main memory (48) and the image processing system (56). The output of the main memory (58) is connected to the input (59) of the image processing system.

In FIG. 4, the cardiac phase-synchronous, three-dimensional images (60 to 64) stored in the main memory (48) are depicted as data cubes of a multitude of voxel. The three-dimensional images (60, 61, 62, 63 and 64) consist of isotropic cubic data sets with each image layer consisting of 256×256 pixel for example. 8 bit may be used to depict the picture half-tone of the scanning elements or voxel.

If the three-dimensional image (60) is stored in the image processing system (56), the image processing system (56) allows for the drawing of an arbitrary section plane (66) through the data set depicted as a cube in FIG. 4 and for the determination of the new sectional image (67). The orientation of the assigned section plane (66) does not necessarily correspond to the relative position of either section plane 36 or 37. The section image (67) can then be transferred to the monitor (31) through an output port (68) of the image processing system (56) and be depicted on its monitor as illustrated in FIG. 4.

We claim:

1. An ultrasound endoscopy device for transesophageal echocardiography, comprising;
    an ultrasound transducer, for scanning a series of parallel section planes of the heart with ultrasonic energy, converting ultrasound scans into electrical signals, the electrical signals being analogs of the scanned series of parallel section planes, and transmitting the electrical signals, the ultrasound transducer being slidably mounted upon a sliding rail situated in the interior of the device, such that the transducer may be linearly moved along the sliding rail of the device;
    ultrasound diagnostic means for receiving analog signals of said series of parallel section planes, converting the analog signals into signals in the form of tomograms and transmitting the signals; and
    an image processing system for receiving the signals in the form of tomograms from the diagnostic means, the image processing system comprising,
        a memory storage buffer capable of storing at least one said tomogram in synchronization with the cardiac phases when scanning each said section plane;
        a main memory for storing at least one three-dimensional image composed of a series of parallel ones of said tomograms;
        data selection and transmission means interconnecting a data output port of said memory storage buffer to a data entry port of said main memory, said data selection and transmission means selecting individual ones of said tomograms assigned to consecutive cardiac cycles and transmitting such to said main memory only in those instances where said individual tomograms correspond to cardiac cycles having the same duration; and
        means for preventing the movement of the ultrasound transducer to the next one of said section planes until a successful transfer of data from said memory storage buffer to said main memory.

2. The ultrasound endoscopy device of claim 1, and further including:
    an ECG recording device for controlling the progressive movement of the ultrasound probe along the sliding rail.

3. The ultrasound endoscopy device of claim 2, wherein:
    said ECG recording device includes a dial gauge for determining the R—R intervals of consecutive cycles as well as the frequency distribution of the duration of the R—R intervals;
    said data selection and transmission means transmits an individual tomogram upon receiving a release signal from said ECG recording device;
    said ECG recording device sends a release signal to said data selection and transmission means when the contents of said memory storage buffer conform to a preselected constant R—R interval.

4. The ultrasound endoscopy device of claim 3, wherein:
    said memory storage buffer has the capacity to store a plurality of said tomograms assigned to different cardiac phases of a cardiac cycle; and
    said data selection and transmission means outputs said multiple tomograms from said memory storage buffer in synchronization with the cardiac phases at each section plane positioning of the ultrasound transducer in a chronological series of said three-dimensional images selected for said main memory, said three-dimensional images corresponding to consecutive phases of a cardiac cycle.

5. The ultrasound endoscopy device of claim 1, and further including:
    a spatial coordinate detector for determining the position of a distal end of the ultrasound endoscope, said distal end being the portion of the ultrasound endoscope in which said sliding rails are contained.

6. The ultrasound endoscopy device of claim 5, wherein:
    said coordinate detector permits recording of a frequency distribution of said positions, and
    said means for preventing the movement provide a release signal only in response to a preselected constant set position of said distal end.

7. The ultrasound endoscopy device of claim 5, wherein the device is carried on a gurney, and:
    said spatial coordinate detector includes two coils positioned at right angles to each other in said distal end, and two alternately aligned induction coils, one of which is embedded in the cover of the gurney and the other in a side wall arrayed at right angles to the surface of the gurney, the combined generated magnetic fields operating to establish a fixed system of coordinates.

8. The ultrasound endoscopy device of claim 1, and further including:
    monitor means for monitoring the respiration pattern of the patient, being connected to said means for preventing movement, said monitor means blocking said movement under conditions where said respiration pattern is unstable.

9. The ultrasound endoscopy device of claim 1, wherein:
    said main memory is controlled by a computer, said computer including display means and being adapted to display said tomograms juxtaposed with said three dimensional images upon said display means.

10. The ultrasound endoscopy device of claim 9, wherein:
    said computer includes programming means for determining and displaying the measurements of the heart, and, in particular, for determining the volumes of the different ventricles of the heart, the thickness of the cardiac wall, the mass of the cardiac muscles, changes in cardiac walls in comparative studies and movements of the cardiac walls during a cardiac cycle.

* * * * *